United States Patent [19]

Takai et al.

[11] Patent Number: 4,721,652
[45] Date of Patent: Jan. 26, 1988

[54] COMPOSITE FOR DECOMPOSING AND ADSORBING UREA DISSOLVED IN LIQUID

[75] Inventors: Nobuharu Takai, Tokyo; Sumio Saitoh, Yokohama, both of Japan

[73] Assignee: Catalysts & Chemicals Industries Co., Ltd., Tokyo, Japan

[21] Appl. No.: 821,082

[22] Filed: Jan. 21, 1986

[30] Foreign Application Priority Data

Jan. 25, 1985 [JP] Japan ................................ 60-13020

[51] Int. Cl.$^4$ .......................... B32B 5/16; C12N 11/14
[52] U.S. Cl. .................................. 428/403; 210/502.1; 210/645; 428/404; 435/176
[58] Field of Search ............... 428/403, 308.4, 404; 210/502.1, 645; 435/176

[56] References Cited

U.S. PATENT DOCUMENTS 3,989,622 11/1976 Marantz et al. ...................... 210/645
4,206,259 6/1980 Rohrbach et al. ............ 428/308.4 X
4,581,141 4/1986 Ash .................................. 210/502.1

Primary Examiner—Thomas J. Herbert
Attorney, Agent, or Firm—Flynn, Thiel, Boutell & Tanis

[57] ABSTRACT

A composite comprising a core of urease-containing particles covered with fine zeolite powders for decomposing urea dissolved in a liquid and adsorbing a product resulting from said decomposition.

13 Claims, 1 Drawing Figure

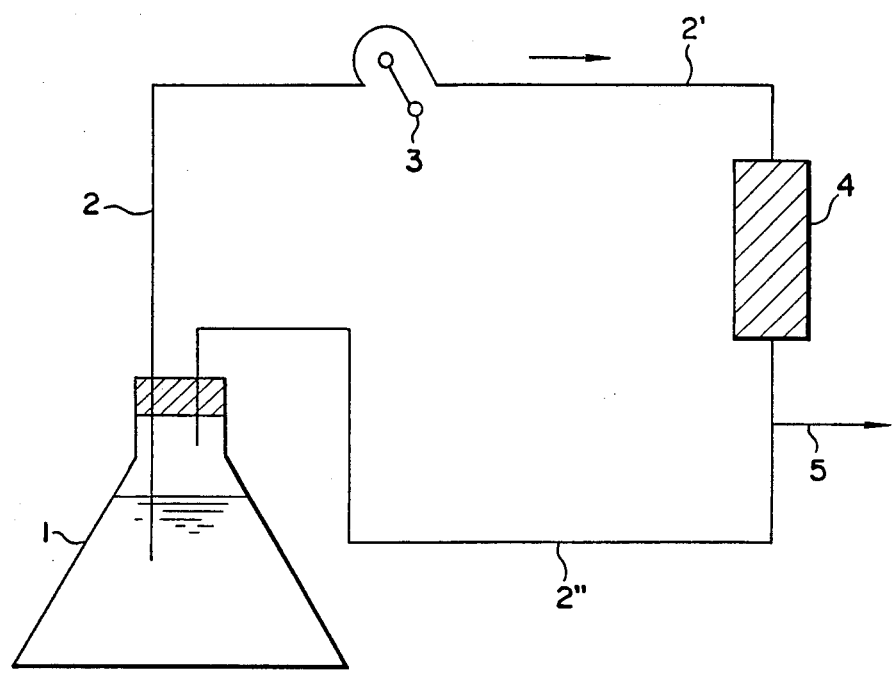

COMPOSITE FOR DECOMPOSING AND ADSORBING UREA DISSOLVED IN LIQUID

The present invention relates to a composite for decomposing and adsorbing urea dissolved in a liquid, said composite comprising covering a particle-shaped urease with a fine zeolite powder. The present invention provides a composite for decomposing the urea existing as a harmful substance in a humor such as blood, plasma, abdominal dropsy or the like or the urea by-produced in a culture solution of a certain kind of cell, in particular, a hybrid cell or the like, and adsorbing the ammonia produced by this decomposition almost simultaneously with decomposition. In more detail, the present invention provides a composite for decomposing and adsorbing urea and is usable as a urea-removing means in artificial organs such, for instance, as artificial kidneys, artificial livers and the like or a urea-removing means attached to cell culture equipment.

It is usual that most patients suffering from kidney diseases such as kidney insufficiency and the like are subjected to artificial dialysis at intervals of several days, though this is variable depending on the condition of kidney insufficiency. This dialysis takes about 3 to 7 hours. Such being the case, the patients suffer not only heavy time-loss from work but also very serious physical and psychological burdens caused by the dialysis itself. In order to remove such burdens and time-loss, there have been proposed artificial organs such as a portable artificial kidney designed to remove harmful ingredient-containing metabolites by the adsorption method or the like, and similarly, an artificial liver and the like. Some of this auxiliary equipment has actually come to be applied for clinical purposes.

In the humor represented by plasma are many harmful metabolites inclusive of urea. The harmful substances exclusive of urea are adsorbed and removed by adsorbents such as activated charcoal and the like to such a degree that no practical problem occurs. However, the adsorbents such as activated charcoal and the like are not superior in the capacity of adsorbing urea. In order to remove urea, therefore, it is necessary to decompose urea and remove ammonia generated at that time. That is, it is necessary to contact a urea-containing solution with a urea decomposable enzyme such as urease for decomposing urea into ammonia and carbonic acid gas, and further to remove this decomposition product by using an absorbent or an ion-exchanged resin or the like.

In view of this, the artificial organ is required to have equipment that is capable of adsorbing normal harmful substances, decomposing urea and adsorbing substances generated from urea decomposition respectively. Accordingly, the fact is that it is difficult to prepare a small-sized artificial organ.

SUMMARY OF THE INVENTION

The present invention provides a particulate composite that is capable of decomposing urea into ammonia and carbonic acid gas by contacting a solution in which urea has dissolved with a urea decomposable enzyme, and adsorbing this decomposition product during said decomposition. This composite comprises covering a core consisting of urease particles with fine zeolite particles.

BRIEF DESCRIPTION OF THE DRAWING

The appended drawing is a schematic diagram of an equipment used in examples referred to afterwards.

DESCRIPTION OF THE PREFERRED EMBODIMENTS

Next, the construction of the particulate composite according to the present invention will be explained concretely, and then its powers of decomposing and adsorbing urea will be shown with reference to its use examples. The isolated urease is very high-priced and, as such, is difficult for practical use in the point of cost. However, in view of the fact that said urease is contained in the seed of Canavalia gladiata in a conspicuously large amount, it is possible to use this powder per se or its refined protein powder as the urease component of the present invention.

The urease particles constituting the core in the composite according to the present invention may be prepared in optional ways. The typical ones will be shown as follows. It is to be noted that the word particle used herein does not always mean "spherical".

Mixed type urease particle

Urease is mixed with powders of silica gel, alumina, inorganic porous sintered bodies, diatomaceous earth and the like. A cellulose system adhesive is added to this mixture, is mixed, and thereafter is dried and milled to thereby prepare a preblend urease powder. The same cellulose system adhesive solution as aforesaid is mixed with this preblend powder, and is extruded into a rod. This rod is cut into proper lengths to thereby prepare pellets. Press molding and roll pelletization may also be employed in place of the extrusion molding. Further, it is employable to extrude into sheets using a T-type die and crush said sheets into flakes. Urease particles are usable in the shape as molded. The desired particle diameter is in the range of 0.1 to 2 mm, preferably in the range of 0.3 to 1 mm. Sieving is sometimes required for that purpose. As the cellulose system adhesive, there may be enumerated an ethanol solution of 4% ethyl cellulose.

Fixed type urease particle

A core was made of an organic substance such, for instance, as a cellulose system, dextran gel and particles obtained by aminopropylizing a silica system porous glass. The surface of this core is reacted with urease in a usual manner, and is fixed. This bond is chemical, but does not so severely influence the enzymatic action of urease. The particle diameter of the core is preferred to be in the same range as that of the mixed type urease particle, irrespective of said core being organic or inorganic.

Impregnated type urease particle

The particle of this type is fixed in the manner of impregnating an aqueous urease solution in pores of a sintered body such as porous silica or porous glass in addition to a porous polymer, vaporizing water at normal temperatures or cooling and drying, and thereafter spraying thereon a diluted solution of a film forming substance such as ethyl cellulose to fix the urease with a thin film of said substance. If said film is thick in this case, there is the possibility of the surface of urease being covered. Attention should be paid to this point.

Embedded type urease particle

This type includes two methods. One method comprises dispersing urease in an aqueous high molecular substance solution or an enzymatic action-maintaining organic solvent solution to obtain an emulsion-polymerized or suspension-polymerized high molecular substance and granulating said substance. The other method comprises dispersing urease i a monomer, mass-polymerizing said monomer, crushing and grading. This embedded type urease particle seems to be complete in the immobilization of the enzyme and higher in activity. If necessary, this may be further coated with cellulose acetate or the like. In this instance, the amount of effective urease seems to be reduced as compared with the total amount of urease used, but there is no practical problem in this respect.

In the present invention, the thus obtained urease particles are covered with zeolite. The zeolite used for covering has a $SiO_2/Al_2O_3$ molar ratio in the range of 2.5–50. Natural zeolite includes mordenite (silica/alumina ratio: about 10), chabazite (silica/alumina ratio: about 5 to 10), erionite (silica/alumina ratio: about 5 to 10) and the like. The synthetic zeolite usable for the present invention includes X- and Y-type ones of mordenite, chabazite or faujasite.

Viewed from the use purpose, however, synthetic zeolite desired contains almost no impurities. The particle diameter of the zeolite used is in the range of about 0.5–2μ. There is a general tendency that in case the silica/alumina ratio is large, the amount of ammonia adsorbed decreases, while the initial rate of adsorption increases.

Next, reference will be made to the means for covering the urease particle with fine zeolite powders. Fine zeolite powders are put in a fluid bed vessel provided at its bottom with a gas permeable porous plate and designed to blow a gas up through said porous plate to thereby form a zeolite fluid bed. In this fluid bed are put urease particles whose surfaces have been wet by spray adhering a dilute organic adhesive solution thereon. The urease particles and fine zeolite powders are thus fluid mixed, and thereafter the urease particles are separated. The surface of the thus obtained urease particle has been covered with fine zeolite particles. However, it is desirable to re-cover the urease particle by the same covering means (which comprises re-wetting the once covered urease particle surface with a dilute adhesive solution so as to promote its mixing and fluidizing with zeolite) because the urease particle surface is sometimes not covered completely owing to collision between urease particles and the like. If necessary, this operation may be further repeated.

Combination of a plurality of covered urease particles can be attained by spray adhering an adhesive solution on the thus obtained zeolite-covered urease particles, stirring these particles properly, drying and sieving.

When it is intended to make a plurality of urease particles exist in a zeolite-covered urea decomposing and adsorbing agent, it may be attained by rolling and grading the urease particles covered once with zeolite together with fine zeolite particles while spraying a dilute adhesive solution. In this instance, the dimensions of the aforesaid combination of a plurality of zeolite-covered urease particles may be determined properly according to its use purpose. In the thus obtained composite for decomposing and adsorbing urea, fine zeolite powders adhere layerwise and closely on the urease particle surface, but this layer freely is penetrated by a liquid. Accordingly, when an urea-containing liquid to be treated is passed through a column charged with the decomposing and adsorbing composite according to the present invention, said liquid penetrates the zeolite layer making contact with the urease, whereby the urea decomposes at once. The ammonia resulting from said decomposition contacts the zeolite layer immediately after its preparation so that the resulting ammonia is adsorbed here by zeolite completely without leakage. The amount of the composite used according to the present invention may be determined beforehand by estimating the amount of urea that said composite can decompose and remove. The use of the composite of the present invention having the function as aforesaid is exceedingly effective because the drawbacks inherent in the usual adhesives such as activated charcoal and the like can be eliminated completely.

Preparation of the composite for decomposing and adsorbing urea

EXAMPLE 1

100 g of reagent urease produced by Hani Kagaku K.K., 250 g of silica gel and 150 g of Absel (trade name of the microcrystalline cellulose produced by Asahi Kasei K.K.) are well mixed. 500 ml of an ethanol solution of 4% ethylcellulose is added little by little to said mixture with mixing, thereby preparing a wet mixture. This mixture is extruded by an extruding machine into a pellet. This pellet is dried and thereafter graded. This is a named a.

According to the exact same procedure, excepting the use of 250 g of zeolite in place of 250 g of silica gel, there is obtained a pellet. This pellet is likewise dried and thereafter graded. This is named b.

A pellet is obtained likewise using 1400 g of urease, 500 g of Absel (micro crystalline cellulose) and 1000 ml of an ethanol solution of 5% ethylcellulose. This pellet is likewise dried and thereafter graded. This is named c.

1000 g of each of the above a, b and c is taken out. This is mixed with 2000 g of zeolite, and rolled while adding 1000 ml of an ethanol solution of 4% ethylcellulose gradually thereto and thereafter pelletized. The thus obtained zeolite-covered particles are mixed again with 200 g of zeolite, and roll-pelletized and dried into particulate composites. There composites are named A, B and C respectively. The zeolite used herein is Y-faujasite having a silica/alumina ratio of 5.0.

EXAMPLE 2

1000 g of a 30% $SiO_2$-containing silica sol and 3000 g of the same urease as used in the preceding example are mixed. This mixture is poured into 5000 ml of acetone, gelled, air-dried and thereafter graded in diameter 1000 g of thus obtained was taken out, mixed with 3000 g of zeolite, and rolled while adding an ethanol solution of 4% ethylcellulose as done in the preceding example and pelletized. This rolling and pelletizing are repeated to obtain particulate composites. The zeolite used herein is the same as used in the peceding example.

Testing device and its usage

The drawing is a schematic view of a testing device for testing the function of the composite for decomposing and adsorbing urea according to the present invention, wherein (1) denotes a flask, (2) (2') (2") denote pipes for circulating a testing solution, (3) denotes a roller pump disposed between pipes (2) and (2'), (4) denotes a column for receiving the decomposing and adsorbing composite disposed between pipes (2') and (2''), and (5) denotes a branch pipe for sampling. The column (4) is arranged to be replaced by those different in volume.

This device is utilized in the manner of putting a physiological saline or animal blood serum containing urea, circulating this testing solution by means of the pump (3), and sampling same after a predetermined time to measure the amounts of urea and ammonia contained in the solution. In test examples referred to afterwards, it is designed to use a flask of 1000 cc and columns that are capable of receiving the decomposing and adsorbing composite in the amounts of 20 g and 100 g.

TEST EXAMPLE—1

100 mg/dl of urea was dissolved in a physiological saline to prepare a test solution. 300 ml of this test solution was put in a flask, and 20 g of Composite A according to Example 1 was charged in a column. Said solution was circulated at the rate of 100 ml/minute, and the test solution was measured after the lapse of 30 minutes and 1 hour respectively to find that after the lapse of 30 minutes, about 90% of the urea disappeared but the existence of ammonia in the solution could not be perceived, and that after the lapse of 1 hour, urea did not exist in the solution and ammonia could not be detected by the usual method. The same test was carried out with Composites B and C of Example 1. No special difference could be found between the results of Composite A and those of Composites B and C.

TEST EXAMPLE—2

The same test as the preceding Example 1, except that the column was replaced by a 100 g-column, was carried out to find that after the lapse of 30 minutes neither urea nor ammonia could be detected in the solution.

TEST EXAMPLE—3

Test was carried out under the same conditions as Test Example 1 by adding 100 mg/dl of urea to the serum of a mongrel dog and charging the column with 20 g of Composite of the preceding Example 2. The test solution after the lapse of 30 minutes was analyzed to find that urea was decomposed almost completely, and ammonia could not be detected. Any substantial change could hardly be perceived in the serum components.

What is claimed is:

1. A particulate composite for decomposing urea dissolved in a liquid into ammonia and carbon dioxide, and adsorbing the ammonia, which comprises: relatively large size urease-containing core particles covered with relatively small size fine zeolite powder.

2. A composite according to claim 1 wherein said zeolite powder is adhered to said urease-containing core particles by means of an organic binder.

3. A composite according to claim 1 wherein said zeolite powder comprises a plurality of layers covering said core particles.

4. A composite according to claim 1 wherein a plurality of said urease-containing core particles are joined together to form a unitary assembly and said assembly is covered by a layer of said zeolite powder.

5. A composite according to claim 1, wherein said urease-containing core particles comprises urease particles mixed with powdered silica gel, powdered alumina, powder of an inorganic porous sintered body or powder of diatomaceous earth.

6. A composite according to claim 1, wherein said urease-containing core particles comprise a particle substrate of dextran gel or particles obtained by amino propylizing a silica porous glass, and urease fixed to the surface of the substrate by a chemical bond.

7. A composite according to claim 1, wherein said urease-containing core particles comprise a substrate selected from the group consisting of porous sintered silica, porous sintered glass and porous polymers, said core particles being impregnated with urease.

8. A composite according to claim 1, wherein said urease-containing core particles comprises urease embedded in a polymerized substrate.

9. A composite according to claim 1 wherein said zeolite has a silica/alumina ratio in the range of 2.5–50 and an average particle diameter in the range of 0.5–2$\mu$.

10. A composite according to claim 9, wherein said zeolite is selected from the group consisting of natural mordenite, natural chabazite, natural erionite, and X and Y-artificial zeolites of mordenite, chabazite and faujasite.

11. A composite according to claim 9 wherein said core particles have diameters in the range of from 0.1–2 mm.

12. A composite according to claim 11 wherein the core particles have diameters in the range of from 0.3–1 mm.

13. A particulate composite for decomposing urea dissolved in a liquid into ammonia and carbon dioxide, and adsorbing the ammonia, comprising: particulate cores of urease-containing material said cores having a particle size in the range of from about 0.1 to about 2 mm, said particulate cores being coated with an adherent covering layer of a multitude of fine particles of zeolite having a particle size in the range of from about 0.5 to about 2 microns.

* * * * *